United States Patent [19]

Staudinger

[11] Patent Number: 5,036,212
[45] Date of Patent: Jul. 30, 1991

[54] METHOD OF AND APPARATUS FOR ANALYZING A SUSPENSION IN A CUVETTE

[76] Inventor: Gernot Staudinger, Messendorfberg 99, A-8042 Graz, Austria

[21] Appl. No.: 513,287

[22] Filed: Apr. 17, 1990

[30] Foreign Application Priority Data

Apr. 18, 1989 [AT] Austria .................................. 926/89

[51] Int. Cl.⁵ ..................... G01N 15/06; G01N 23/06; G01N 21/01
[52] U.S. Cl. ...................................... 250/575; 378/53; 356/441
[58] Field of Search ................ 250/573, 575; 356/441, 356/442; 378/57, 53, 55, 51; 73/32 R

[56] References Cited

U.S. PATENT DOCUMENTS 4,539,649  9/1985  Michaelis et al. ..................... 378/53
4,775,991 10/1988  Staudinger et al. ................... 378/53

OTHER PUBLICATIONS

Partikelgrossenanalyse SEDIMENTATIONSANALYSE Grundlagen, DIN 66 111, Entwurf Nov. 1983, Normenausschuss Siebboden und Kornessung-(NASK) im DIN Deutsches Institut fur Normung e.V., pp. 1-9.

Primary Examiner—David C. Nelms
Assistant Examiner—La Charles P. Keesee
Attorney, Agent, or Firm—Herbert Dubno

[57] ABSTRACT

Agglomeration or solubilization of particles of a suspension can be determined during a scanning sedimentation analysis of particle-size distribution by monitoring respective values of extinction determined in two successive scans or from one scan and a fixed light curtain at a common ratio h/t where h is the distance of the measurement by the light curtain from the surface of the suspension and t is the time at which the measurement is taken.

8 Claims, 5 Drawing Sheets

METHOD OF AND APPARATUS FOR ANALYZING A SUSPENSION IN A CUVETTE

FIELD OF THE INVENTION

My present invention relates to the analysis of a suspension of sedimenting particles in a liquid suspending medium in a cuvette and, more particularly, to an analysis of such a suspension to determine particle character, i.e. characteristics of the particles in the suspension, namely, their agglomeration and dissolution characteristics, or thermally-induced liquid movement. More particularly, the invention relates to a method of detecting and evaluating agglomeration of particles, dissolution of particles and/or thermally induced liquid movement in a suspension, hereinafter collectively referred to as "stability" of the suspension, and to an apparatus for carrying out this method.

BACKGROUND OF THE INVENTION

Sedimentation is a widespread technique utilized in particle-size analysis and reference may be had, for example, to the discussion of the state of the art of such techniques in U.S. Pat. No. 4,775,991, commonly owned with the present application, the prior art and literature cited therein, and the original techniques described for such analysis in that patent.

A precondition for precise results is a perfect dispersion of the particles in the suspension at the beginning of the measurement process and the absence of effects which alter the particle size or the settling velocity of the particles in the liquid phase or a slow movement of the liquid phase while the measurement is going on.

Such effects could include dissolution, i.e. the dissolving of material from the particles into the liquid phase when the latter functions as a solvent, and agglomeration of the particles, i.e. the mechanical, chemical or electrostatic adhesion of discrete particles together to form a larger agglomerated particle. Another effect which disturbs the sedimentation analysis is circulation of the liquid which may be induced by buoyancy effects, such as differences in density due to temperature or an inclined (not vertical) positioning of the cuvette. This movement of the liquid is called thermal circulation.

The dispersion of the particles in the liquid phase before commencement of a measurement is effected as a rule by ultrasonic and mechanical agitation of the suspension. While the dissolution of the particles in the liquid phase, even when the latter is a solvent for the material of the particles, can be suppressed or minimized by a prior saturation of the solvent with the material before commencement of the measurement, the suppression of agglomeration requires special and more complex precautions during the measurement process.

According to German Industrial Standard DIN 66 111, for example, a variety of suspension liquids are prescribed for the various powders and certain dispersion agents (surfactants or dispersants) are likewise mandated or suggested to maintain the particles in discrete or nonagglomerated form in the liquid. The concentration of the particles in the liquid phase is also limited. In practice it has been found that the conditions of this German Industrial Standard cannot always be achieved and thus, for powders not named in the German Industrial Standard, there is a continuing search for dispersing agents which may be effective.

With particle-size measuring devices which operate very rapidly, for example in accordance with the light-scattering principle, the development of agglomeration can be directly followed when it occurs by monitoring the change in the nature of the particles in the suspension in periods of seconds to minutes.

Attached hereto is a FIG. 1 which shows the measured particle size for a suspension after termination of ultrasonic dispersion and without ultrasonic dispersion, respectively, and can be considered to represent the agglomeration with time.

A sedimentation analysis normally requires at least several minutes and may require up to several hours. As a consequence of the agglomeration during the measuring process, the proportion of small particles in the particle total is reduced while the frequency of medium-size particles is increased. The proportion of very large particles does not normally or necessarily change because these tend to sediment out rapidly and before agglomeration has had a substantial effect on the particle-size distribution.

Thermal circulation in general does not affect the larger materials which have a high sedimentation velocity but does affect the small particles which settle very slowly. If they are very small, their settling velocity is less than the circulation velocity of the liquid. Hence with thermal circulation the measured transmission will be less than in the ideal case.

I have discovered that it is possible to quantify or evaluate this change in the character of the particles, namely, dissolution agglomeration or thermal circulation, in a unique manner so as to enable the new procedure to be used for the analysis and evaluation of the agglomeration, dissolution or thermal circulation, or, if desired, to correct sedimentation analysis for the stability of the suspension.

OBJECTS OF THE INVENTION

It is, therefore, the principal object of the present invention to provide an improved method of determining (detecting) and quantifying the change occurring in a suspension by agglomeration, and, if desired, dissolution, or thermal circulation, i.e. the stability of the suspension.

Another object of this invention is to provide an improved method of analyzing the agglomeration or dissolution of particles in a suspension.

Yet another object of the invention is to test whether the suspension in a cuvette is stationary or in motion.

It is also an object of the invention to provide an apparatus for carrying out the improved method.

SUMMARY OF THE INVENTION

In principle the present method for evaluating a change in characteristics of the particles of a suspension in a cuvette or the stability of the suspension, specifically by the solubilization of the material from the particles or agglomeration, or thermal circulation of the whole suspension, is effected in accordance with the invention by subjecting the cuvette to analysis utilizing a radiation source and sensor combination defining a light curtain or light beam as these concepts are set forth, for example, in U.S. Pat. No. 4,775,991, by scanning the cuvette over its height with such a light curtain or beam, and measuring the extinction of the radiation resulting from the interaction of the beam and the particles of the suspension.

The term "extinction" is here used to refer to "attenuation" of any type, namely, simple obstruction by the particle cross section, light scattering or absorption, depending upon the radiation used and, of course, is mathematically equivalent to a measurement of the transmitted radiation as detected by the sensor since the incident radiation is equal to the sum of the attenuation and the transmission.

According to the invention, a second measurement is made at the same quotient h/t where h is the distance from the top of the suspension in the cuvette and t is an elapsed time since the beginning of the measurement, i.e. the start of the sedimentation. The beginning or start of sedimentation coincides with the end of agitation.

By comparing the values of extinction (attenuation) or transmission from the two measurements having the same quotient or ratio h/t, I am able to ascertain the change in the particles resulting from agglomeration or solubilization or both and to thereby measure agglomeration if solubilization is excluded by prior saturation of the liquid phase. In the same way I can determine whether thermal circulation has occurred during the measurement.

The method of the invention, more particularly, can comprise the steps of:

(a) introducing the suspension into a cuvette transmissive to a radiation capable of obstruction by the particles;

(b) scanning the suspension in the cuvette over a height h thereof as measured from the top of the suspension in the cuvette and a time t measured from the beginning of the sedimentation of the particles in the suspension in the cuvette with a beam of the radiation and simultaneously measuring radiation of the beam transmitted through the suspension to establish first measured values of radiation extinction or transmission corresponding to various ratios h/t;

(c) separately measuring at least one further value of extinction of transmission at least at one corresponding ratio h/t;

(d) comparing a first measured value at a given ratio h/t from step (b) with the further value at the given ratio h/t in step (c); and (e) relating a difference resulting from comparison in step (d) of the first measured value at the given ratio h/t from step (b) with the further value at the given ratio from step (c) to determine a change in character of the particles of the suspension or thermal movement of the suspension.

An apparatus for carrying out the method can comprise:

a cuvette transmissive to a radiation capable of obstruction by the particles receiving the suspension;

means for scanning the suspension in the cuvette over a height h thereof as measured from the top of the suspension in the cuvette and a time t measured from the beginning of sedimentation of the particles in the suspension in the cuvette with a beam of the radiation and simultaneously measuring radiation of the beam transmitted through the suspension to establish first measured values of radiation extinction or transmission corresponding to various ratios h/t;

means for separately measuring at least one further value of extinction of transmission at least at one corresponding ratio h/t;

means for comparing a first measured value at a given ratio h/t with the further value at the given ratio h/t; and means for automatically relating a difference resulting from comparison of the first measured value at the given ratio h/t with the further value at the given ratio to a change in character of the particles of the suspension or thermal movement of the suspension.

Of course, while the method and apparatus have been phrased in terms simply of analyzing agglomeration, solubilization and thermal movements in sedimenting particles in suspension, the measurements may also be used to correct sedimentation rate determinations of particle size.

In German open application DE-OS 36 18 707, there is described a process and an apparatus for particle-size analysis in which the progress of sedimentation is measured by a plurality of such light curtains disposed one above another (see also U.S. Pat. No. 4,775,991).

The spacing of the light curtains from the surface of the suspension is optimized according to a set of rules described in this printed application. Each of the sensors supplies in principle the same information in the form of a relationship between extinction (attenuation) and time at predetermined sedimentation heights $h_1$, $h_2$, $h_3 \ldots h_N$, but at a different level or distance $h_1$, $h_2$, etc., from the upper surface of the suspension and at the respective time $t_1$, $t_2$, $t_3 \ldots t_n$ after the beginning of sedimentation. The time of the measurement at each height is treated as proportional to the height (for example $t_{1'} = t \times h_3/h_1; t_{2'} = t \times h_3/h_2; \ldots$), and in an ideal case, the measured curves can be expected to correspond to those shown in FIG. 2.

Surprisingly, however, this is often not the case. The origin of the discrepancy, I have discovered, can be attributed only to a change in the particle distribution of the suspended particles during the measurement interval or to thermal circulation. Furthermore, I have also found that the possible changes are due to changes resulting from solubilization of the particles in the liquid and thus their optical or radiation/obstruction "disappearance" or to agglomeration, both dissolution and agglomeration change the settling velocity of the particles, and—like thermal circulation—cause an incorrect particle size measurement.

As I have indicated, the solubilization of the particles during the measurement interval can be easily prevented during the measurement interval by saturating the liquid phase with the material of the particles or by selecting a liquid in which the particles are completely insoluble. Since these techniques may not always be available, the solubilization can be evaluated and the contribution to the disparity in the two measurements can be determined by repeating the measurement with intervening dispersion and agitation of the particles to break up the agglomerates which have possibly formed.

Since the starting conditions of the two runs must be identical in the absence of dissolution of the particles, any difference at the commencement of the measurements can be attributed to solubilization of material of the particles. This effect can be observed as a greater transmissivity through the cuvette of the suspension at the commencement of the second measurement.

Agglomeration cannot, however, be readily monitored in a sedimentometer of the type previously described since, firstly, the agglomerates which are formed are very fragile and are readily broken up by even simple stirring which is commonly carried out in every sedimentation analysis and is the reason why repeat measurements are assured of beginning with the same particle-size distribution as the original measurement, except for the solubilization effected noted above, and secondly, agglomeration processes are surprisingly well reproducible so that a repeat measurement on the same suspension generally shows the same particle size distribution. Thus even if a large number of measurements are taken with prior agitation, practically the same results are obtained although these results may be false as far as particle-size measurements are concerned because of the agglomeration processes.

For the user of sedimentation analysis, however, it is important to determine whether agglomeration is occurring during the process and what the effect of that agglomeration is. If agglomeration is occurring, then the particle-size measurement obtained by sedimentation analysis is false. One, knowing that agglomeration is occurring and desirous of accurate results by sedimentation analysis, can select another dispersing liquid and/or a different dispersing agent or elect to use a surface-active agent promoting dispersion to avoid agglomeration in that case.

In sedimentation analysis thermal circulation should be zero. With a conventional sedimentometer, having one stationary sensor or one scanning sensor shows circulation cannot be detached because the particles settle faster than the circulation velocity. With multiple measurement of the transmission at equal h/t the transmission values are not equal if circulation has occurred.

I have discovered, quite surprisingly, that using a sedimentometer of the type described in the above-mentioned German open application and U.S. patent having a plurality of light curtains arranged one above the other, an indication of agglomeration can arise from the noncoincidence of the successive transmission curves if the powder in suspensions has agglomerated. With a sedimentometer having a single light curtain, this is not possible since only a single extinction/height (time) curve is generated. The same drawback characterizes a so-called scanning sedimentometer wherein a single light curtain is moved along the cuvette or is held stationary while the cuvette is displaced to sweep the beam over the height of the cuvette.

Hence the present invention provides the second measurement as described. According to a feature of this invention, the further value is obtained by sweeping the suspension in the cuvette over the height h thereof and time t with the beam of the radiation and simultaneously measuring radiation of the beam transmitted through the suspension to establish further measured values of radiation extinction or transmission corresponding to various ratios h/t.

Alternatively, the further value is obtained by passing another beam of the radiation through the suspension in the cuvette at a fixed value h of the height and simultaneously measuring radiation of the beam transmitted through the suspension to establish further measured values of radiation extinction or transmission corresponding to various ratios h/t over time t.

When the transmission values at the same h/t are not equal, this fact can lead to the interpretations as follows:

If the later-measured transmission at a given h/t is smaller ($E_1/E_2 > 1$) then agglomeration and/or solubilization can be affecting the result.

If the later-measured transmission at a given h/t is greater ($E_1/E_2 < 1$) then thermal circulation can be affecting the result.

The method of the invention can further comprise the steps of storing respective values of the difference between transmission and extinction values ($E_1$, $E_2$) corresponding to a range of values of agglomeration solubility and thermal circulation of the particles at various h/t ratios, and relating a difference resulting from comparison in step (d) of the first measured value at the given ratio h/t from step (b) with the further value at the given ratio from step (c) to a change in character of the particles of the suspension comprising the step of retrieving a respective value of the agglomeration/solubilization or thermal circulation corresponding to a difference derived by the comparison.

While a difference in the two measurements will indicate that thermal circulation, agglomeration and/or solubilization is occurring, the size of the difference will indicate whether it is thermal circulation or agglomeration/solubilization, and the magnitude of this difference will represent a measurement of the degree of agglomeration and/or solubilization or thermal circulation, it is possible to relate that difference to previously stored values of the measured attenuations at the same quotients h/t by drawing upon previously stored values relating attenuation differences and agglomeration/solubilization or thermal circulation in a table, e.g. via the memory of a computer.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
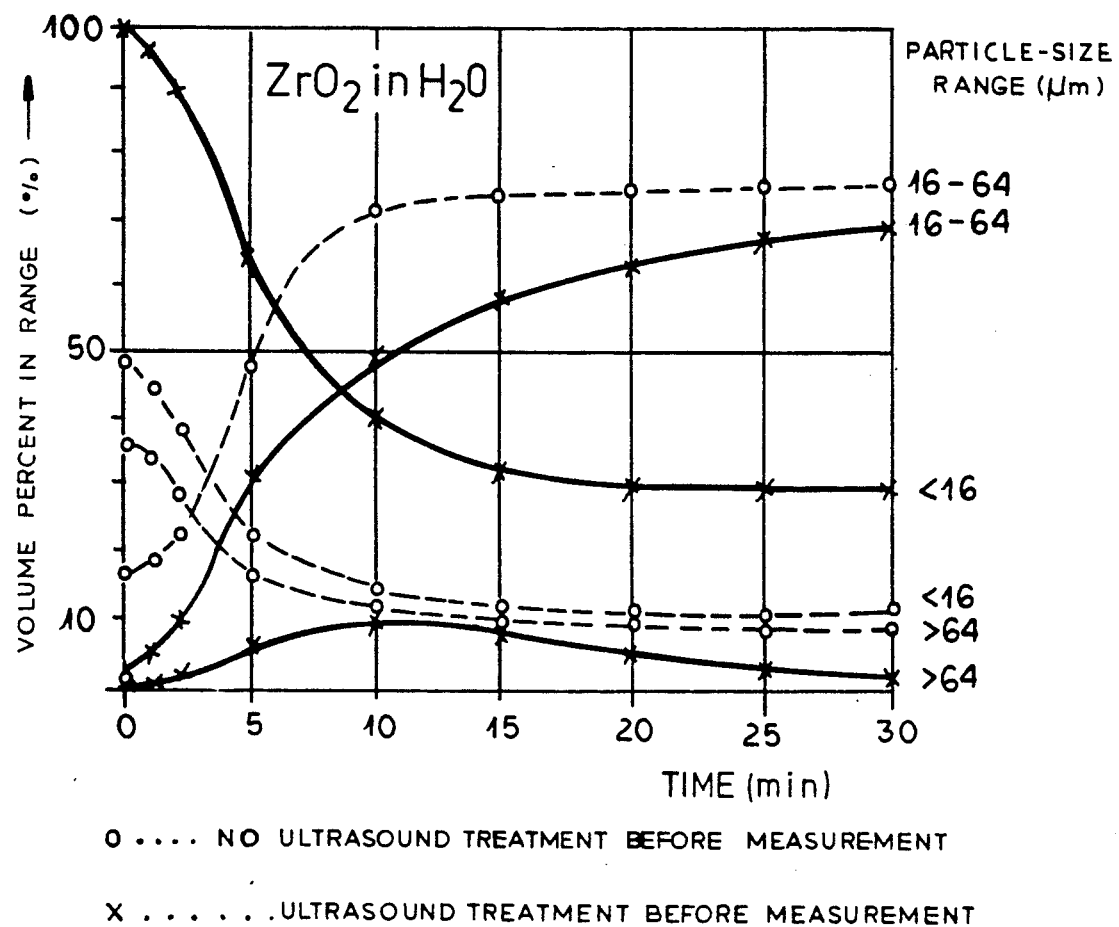
FIG. 1 is a graph relating sedimentation and time for a suspension of zirconium dioxide in water.
Figure 2:
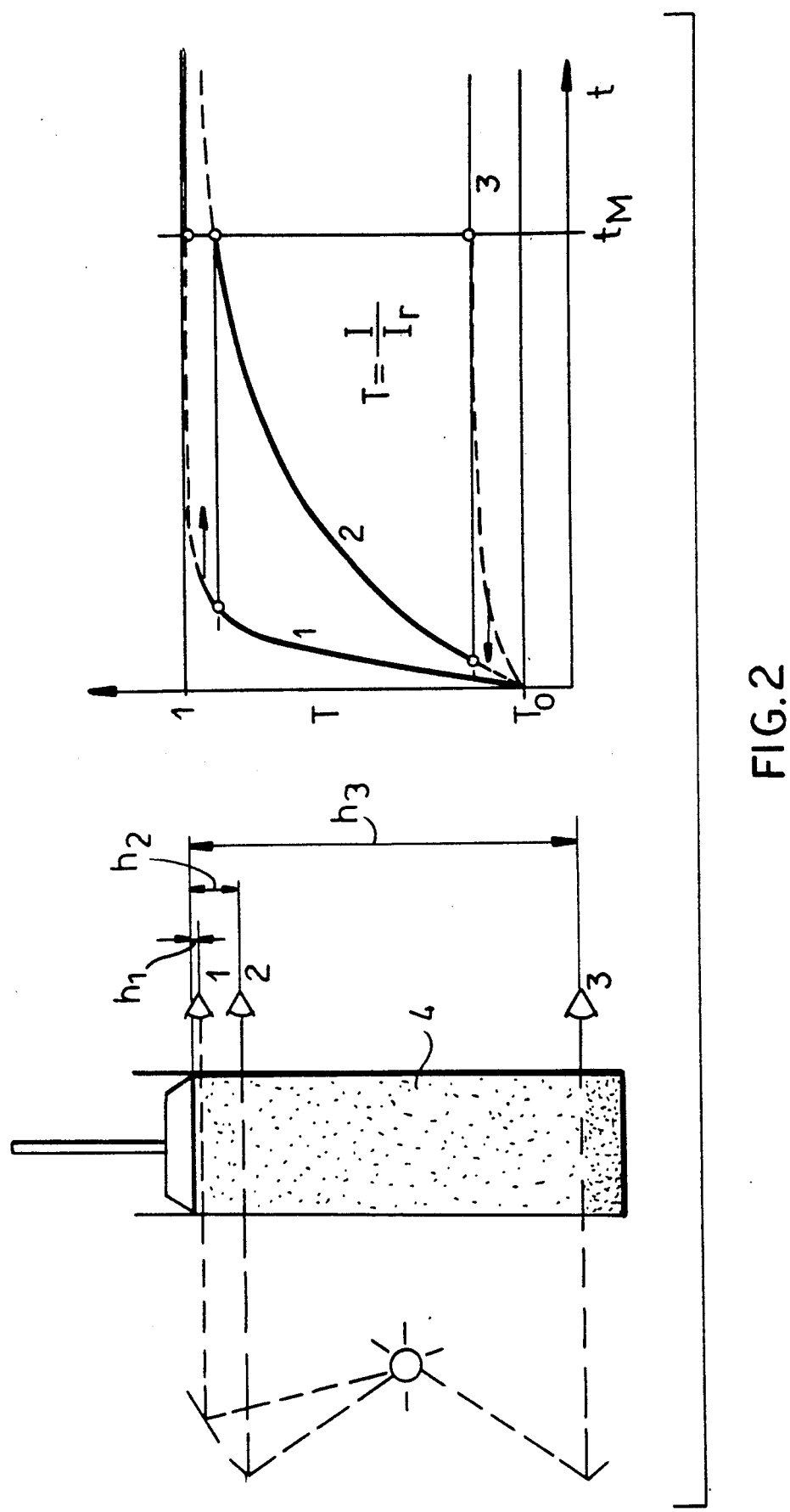
FIG. 2 is a diagram showing the sedimentation curves as measured at various heights along a cuvette and relating these heights to the cuvette, the curves being normalized to the distance $h_2$ at which the measurement is taken below the upper level of the suspension.
Figure 3:
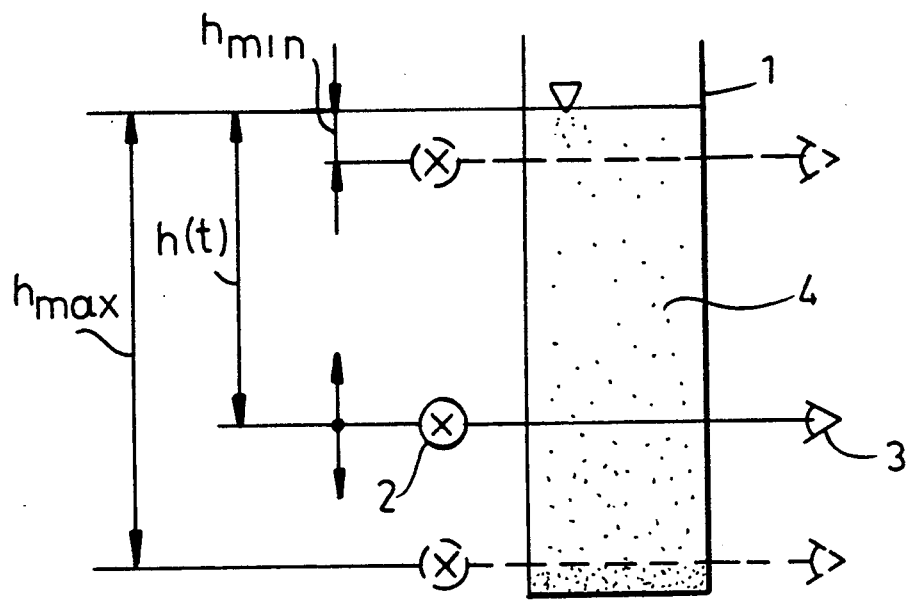
FIG. 3 is a diagram illustrating the invention.

In FIG. 3 I have shown a cuvette 1 whose walls are transparent to the type of radiation used in the scanning sedimentometer. The radiation which can be used is described in U.S. Pat. No. 4,775,991, for example. The scanning light curtain is formed from a sensor 3, responsive to the intensity of the transmitted radiation, and a radiation source 2 capable of emitting that radiation in a beam trained upon the sensor 3. In the cuvette 1 a suspension 4 is shown which has a fixed upper level.

The light curtain 2, 3 is movable between levels $h_{min}$ and $h_{max}$ to thereby scan the suspension. At $h_t$, I have represented the distance of the light curtain below the level of the suspension 4 in the cuvette at the time t. The agglomeration/solubility or thermal circulation test, utilizing a second scan for the second measurement or a second light curtain for the second measurement is independent of the type of radiation (x-ray, gamma ray, light, etc.) utilized for the particular beam.

Light radiation has been found to be especially effective for the detection of agglomeration and solubilization because the signals which result are proportional to the cross-sectional areas of the particles. X-ray and gamma ray radiation are absorbed in proportion to the molecular mass of the material constituting the particles and are less effective, especially in the case of hard radiation for the measurement or detection of agglomeration.

Figure 6:
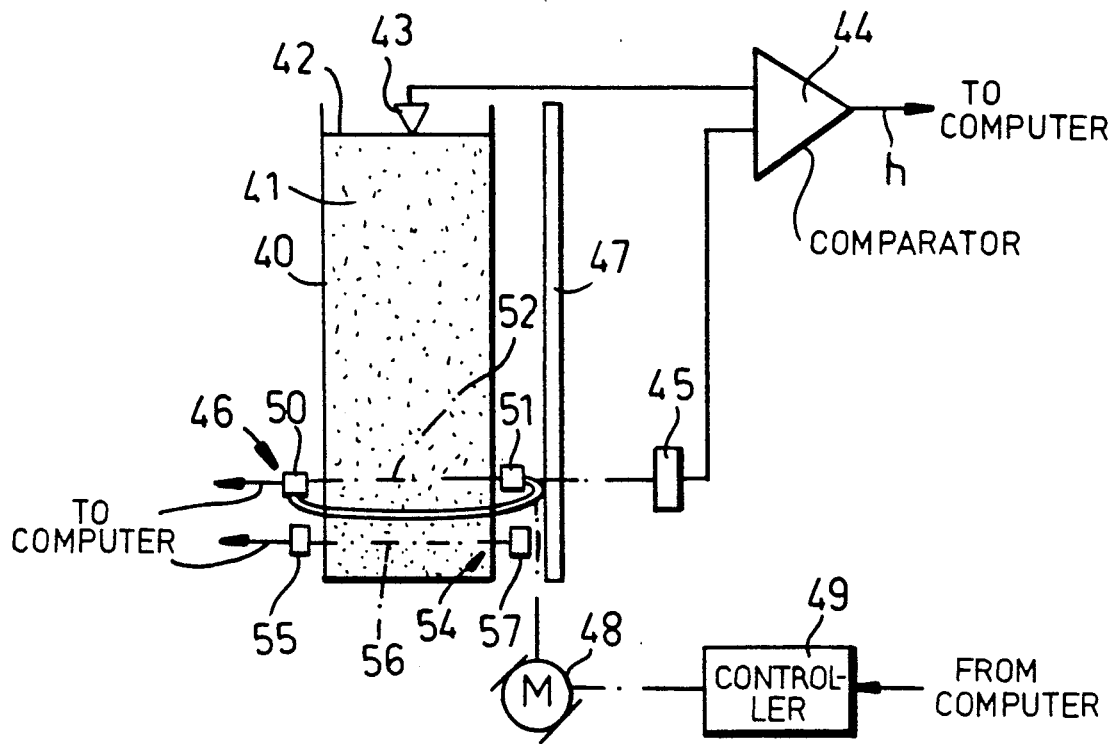
FIG. 6 is a diagram of a scanning sedimentometer for use in the method of the invention.

When the light curtain is moved upwardly along the cuvette, e.g. via the means shown in FIG. 6, or is swept along the cuvette because the latter is drawn downwardly through the light curtain, at each level of the cuvette only a single measured value for the extinction or attenuation is obtained at this location at a respective time corresponding to the state of the suspension at that location as traversed by the light beam at that time. This information suffices to allow a determination of the particle-size distribution for unchanging particles. From these values alone, the presence or absence of agglomeration or the degree of agglomeration or dissolution cannot be determined.

Thus a further piece of information is required as noted. This can be obtained by introducing a second light curtain which can measure the suspension in the measurement range of the movable sensor, so that the principle of plural light curtains, as in the device of German open application 36 18 707 or U.S. Pat. No. 4,775,991, can be used. However, it is less expensive to utilize the movable sensor to provide two measurements without intervening agitation. In this case, the information is obtained in the form of two extinction or attenuation/time (height) curves which do not coincide.

If the curves do not coincide, the difference in the attenuation values at the same ratio h/t represents a change in the suspension in the intervening time, for example, solubilization or agglomeration of the particles or circulation of the suspension.

The type and manner of the two measurements can vary to suit particular requirements.

In one case, the first measurement, for example the determination of the particle-size distribution, is carried out in the manner described and then the second measurement is obtained by repeating the process without intervening agitation. The two attenuation/height (time) curves must coincide after mechanical processing if there is no agglomeration or dissolution or circulation and the difference as described represents the degree of particle change.

A second technique affects the first measurement by movement of the light curtain from the greatest height $h_{max}$ to the smallest height $h_{min}$ and is followed by a movement back to the greatest height $h_{max}$ and a measurement of the attenuation for the second value. The measurements are compared with respect to the ratio h/t and a deviation at a given ratio of the two measurements signals instability of the suspension.

In a third approach, the smallest measurable particle diameter is determined at the end of the measuring time $t_{max}$ at the minimal height $h_{min}$ of the sensor. The largest measurable particle diameter is determined at the greatest height $h_{max}$ and the shortest measuring times $t_{min}$. The sensor and light curtain are then moved twice from $h_{max}$ to $h_{min}$. The overall measuring procedure is not lengthened with respect to earlier methods and nevertheless provides the two measured values which can be handled as described above.

For the measurement of the particle-size distribution the two measurement curves can be combined as described, for example, in German open application 36 18 707.

The mathematical handling of the measurement curves of a sedimentometer with a plurality of sensors or successive measurements in time of a single scanning sensor to test for agglomeration or circulation can be effected as follows.

In the sedimentation analysis one starts from the proposition that each particle has a velocity with which it settles in the liquid that corresponds to its diameter and that this velocity is constant. As a consequence, the extinction (or transmission, since $E = -\ln T$, where E is the extinction and T the transmission) at a height $h_1$ (distance from liquid surface) can be measured at a time $t_1$ and at another height $h_2$ at a time $t_2 = (h_2/h_1) \times t_1$, i.e. E is a function of $h_n/t_n$ and must be equal for equal quotients $h_n/t_n$. This scanning sedimentometer must register the extinction, height and time. The difference in the values $E_1$ and $E_{1'}$ for the first and second measurements for a given ratio $h_n/t_n$ represents instability as caused by agglomeration solution or circulation which is thus detected by this test of the difference.

Figure 4:
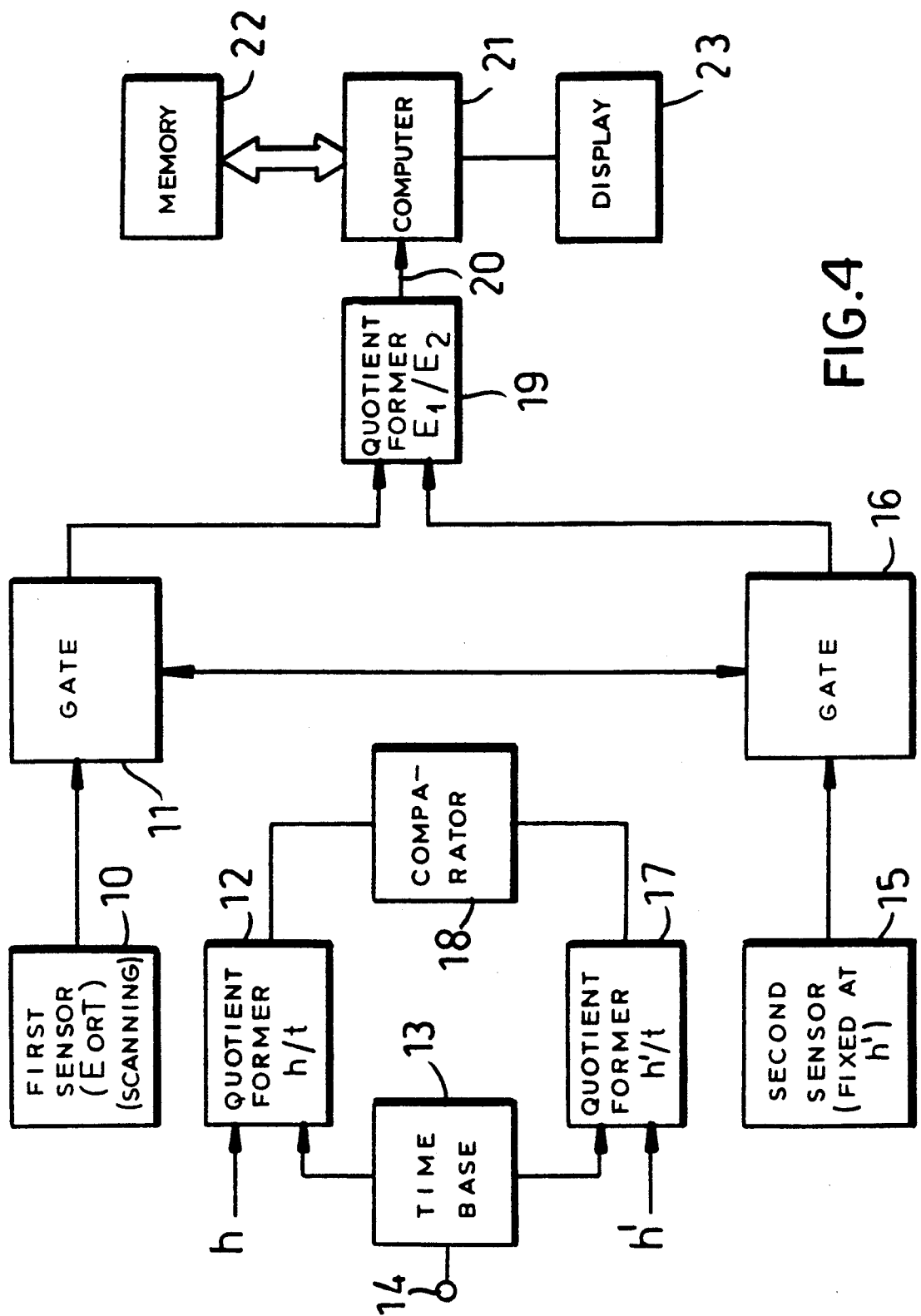
FIG. 4 is a block diagram illustrating an apparatus for determining agglomeration using the principles of the present invention.

In FIG. 4 I have shown a system which exploits this phenomenon. A light curtain 10 generates a value of the attenuation or transmission and provides an input to a gate 11. The height h of the scanning sensor 10 is fed to a quotient former 12 to which is fed a timing signal from a time base 13 which has to be started at the start of the sedimentation (which coincides with the end of stirring the suspension in the cuvette) by an input at 14. In the quotient former 12, therefore, a value h/t is obtained for the first measured value (E or T) outputted from the sensor 10. A second sensor, e.g. one fixed at a level h' within the scanning range of the first sensor, is represented at 15 and provides an input to the gate 16.

Similarly, a quotient former 17 receives a reference input h' representing the level of the second sensor and an input from the time base 13 to produce the quotient h'/t.

The outputs from the quotient formers 12 and 17 are applied to a comparator 18 which delivers its output when the two quotients are equal to trigger the gates 11 and 16 to deliver their respective extinction values to a quotient former 19. The quotient of the extinction values $E_1/E_2$ for the given quotient h/t can then be used to signal the operator that instability is effecting the sedimentation analysis. It may be fed at 20, for example, to a computer 21 capable of scanning its memory 22 for stored values of the quotient $E_1/E_2$ associated with that particular agglomeration value to provide a quantitative display at 23 of the degree of agglomeration or dissolution or circulation.

When $E_1$ is the extinction of an earlier measurement and $E_2$ is the extinction of a later measurement for a given h/t, the quotient $E_1/E_2$ indicates on the one hand whether agglomeration or solubilization or on the other hand whether thermal circulation is occurring. If this quotient $E_1/E_2 > 1$ then agglomeration or solubilization is occurring. If $E_1/E_2 < 1$ then circulation is affecting the result.

Figure 5:
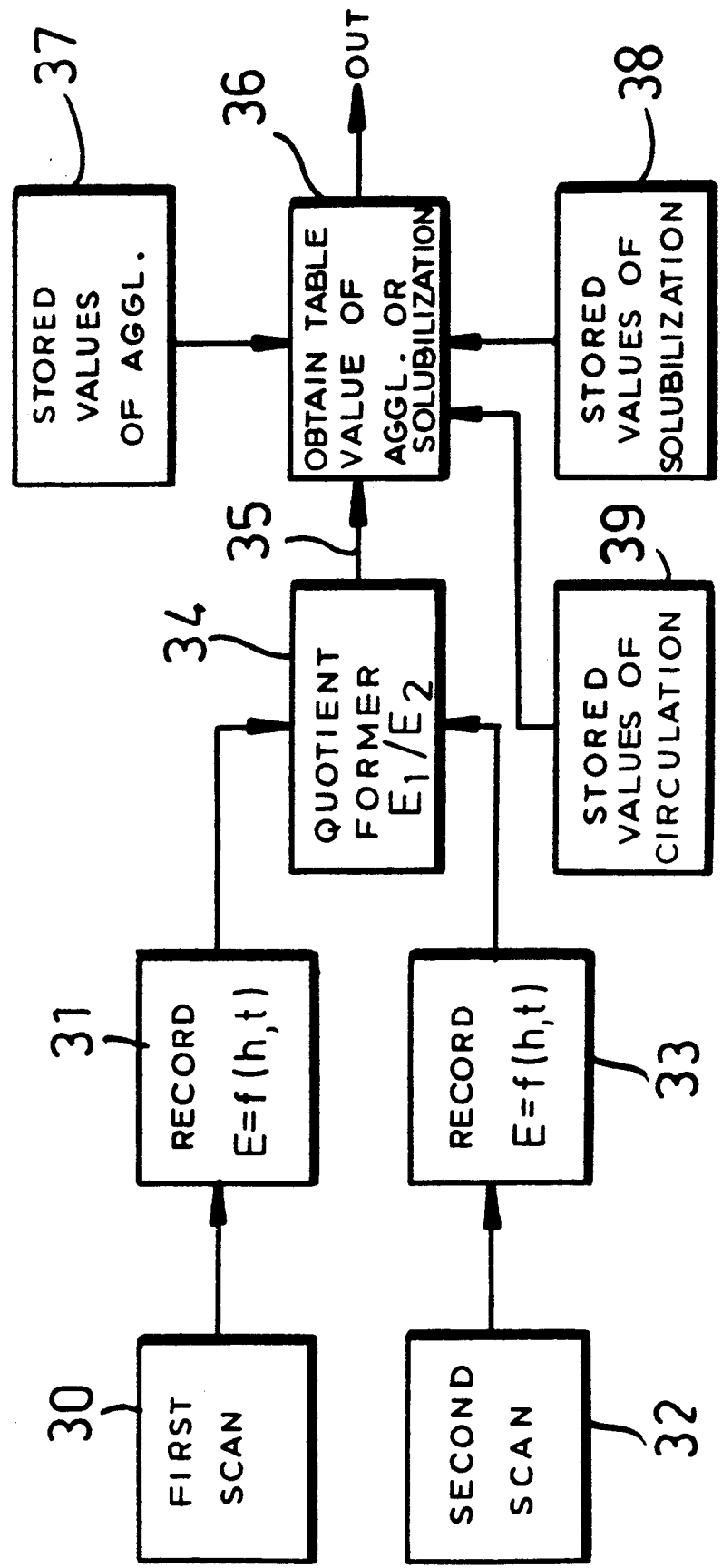
FIG. 5 is a process block diagram of the invention.

The method illustrated in FIG. 5 is the double-scan method discussed above. The first scan at 30 records the extinction value E as a function of h and t at 31 in the aforementioned extinction curve. The second scan at 32 provides registration at 33 of a second curve $E_2$ as a function of h and t.

From the values $E_1$ and $E_2$ the quotient $E_1/E_2$ is formed at 34 and an output is provided at 35 in the event the quotient differs from unity at the same quotient h/t. This output can be used at 36 to obtain from a table of stored values at 37 or 38, a value of agglomeration or solubilization yielding the difference in the extinction values for the given quotient. Stored values 39 of thermal motion can also be provided.

In FIG. 6 I have illustrated highly diagrammatically a cuvette 40 containing a suspension 41 to a level 42 which can be measured at 43 to provide a reference level for determination of the value h by a comparator 44 receiving its other input from a position sensor 45 monitoring the position of the scanning radiation curtain 46 along the cuvette. The scanning radiation curtain can be displaced along a rail 47 by a motor 48 whose controller 49 receives an input from the computer, for example to initiate the second scan.

The radiation curtain 46 can comprise a sensor 50 in line with a source 51 of the radiation so as to generate a beam 52 through the cuvette. The source and sensor can be provided on a common yoke 53.

The additional radiation curtain 54 can be provided within the measuring range of the radiation curtain 46. For convenience of illustration, the two radiation curtains have been shown in the same plane but generally the radiation curtain 54 will be offset angularly from the radiation curtain 46 about a vertical axis of the cuvette to allow it to be cleared by the scanning radiation curtain.

The radiation curtain 54 comprises a sensor 55 for the beam 56 of radiation from the source 57. The radiation curtain 46 thus provides the first value of the extinction while the radiation curtain 54 provides the second value of the extinction at the given ratio h/t as described above.

I claim:
1. A method of determining stability of a suspension which can be affected by agglomeration, dissolution and thermal movement of particles of the suspension, comprising the steps of:
   (a) introducing said suspension into a cuvette transmissive to a radiation capable of obstruction by said particles;
   (b) scanning said suspension in said cuvette over a height h thereof as measured from a top of said suspension in said cuvette and a time t measured from the start of the sedimentation of said particles in said suspension in said cuvette with a beam of said radiation and simultaneously measuring radiation of said beam transmitted through said suspension to establish first measured values of radiation extinction or transmission corresponding to various ratios h/t;
   (c) separately measuring at least one further value of extinction or transmission at least at one corresponding ratio h/t;
   (d) comparing a first measured value at a given ratio h/t from step (b) with said further value at said given ratio h/t in step (c); and
   (e) relating a quotient resulting from comparison in step (d) of said first measured value at said given ratio h/t from step (b) and said further value at said given ratio from step (c) to said stability of said suspension.

2. The method defined in claim 1 wherein said further value is obtained by sweeping said suspension in said cuvette over said height h thereof and time t with said beam of said radiation and simultaneously measuring radiation of said beam transmitted through said suspension to establish further measured values of radiation extinction or transmission corresponding to various ratios h/t.

3. The method defined in claim 1 wherein said further value is obtained by passing another beam of said radiation through said suspension in said cuvette at a fixed value h of said height and simultaneously measuring radiation of said beam transmitted through said suspension to establish further measured values of radiation extinction or transmission corresponding to various ratios h/t over time t.

4. The method defined in claim 1, further comprising the step of storing respective values of said quotient corresponding to a range of values of agglomeration of said particles, the step (e) of relating a quotient resulting from comparison in step (d) of said first measured value at said given ratio h/t from step (b) and said further value at said given ratio from step (c) to a change in character of said particles of said suspension comprising the step of retrieving a respective value of said agglomeration corresponding to a difference derived by said comparison.

5. The method defined in claim 1, further comprising the step of storing respective values of said quotient corresponding to a range of values of dissolution of said particles, the step (e) of relating a quotient resulting from comparison in step (d) of said first measured value at said given ratio h/t from step (b) and said further value at said given ratio from step (c) to a change in character of said particles of said suspension comprising the step of retrieving a respective value of said dissolution of said particles corresponding to a quotient derived by said comparison.

6. An apparatus for determining stability of a suspension which can be effected by agglomeration, dissolution and thermal movement of particles of a suspension, comprising:
   a cuvette transmissive to a radiation capable of obstruction by said particles receiving said suspension;
   means for scanning in vertical direction said suspension in said cuvette over a height h thereof as measured vertically downward from a top of said suspension in said cuvette and a time t measured from the start of sedimentation of said particles in said suspension in said cuvette with a beam of said radiation and simultaneously measuring radiation of said beam transmitted through said suspension to establish first measured values of radiation extinction or transmission corresponding to various ratios h/t;
   means for separately measuring at least one further value of extinction of transmission at least at one corresponding ratio h/t;
   means for comparing a first measured value at a given ratio h/t with said further value at said given ratio h/t; and
   means for automatically relating a quotient resulting from comparison of said first measured value at said given ratio h/t and said further value at said given ratio to said stability of said suspension.

7. The apparatus defined in claim 6 wherein said means for separately measuring said further value includes means for scanning said suspension in said cuvette over said height h thereof and time t with said beam of said radiation and simultaneously measuring radiation of said beam transmitted through said suspension to establish further measured values of radiation extinction or transmission corresponding to various ratios h/t.

8. The apparatus defined in claim 6 wherein said means for separately measuring said further value includes means for passing another beam of said radiation through said suspension in said cuvette at a fixed value h of said height and simultaneously measuring radiation of said beam transmitted through said suspension to establish further measured values of radiation extinction or transmission corresponding to various ratios h/t over time t.

* * * * *